United States Patent
Holekamp et al.

(10) Patent No.: US 11,654,049 B2
(45) Date of Patent: May 23, 2023

(54) INSTRUMENT FOR ISOLATING CANDIDATE EYELASHES TO ATTACH PROSTHESES

(71) Applicant: DEL, LLC, Saint Louis, MO (US)

(72) Inventors: Nancy M. Holekamp, Saint Louis, MO (US); Rita E. Hindmon, Florissant, MO (US); Michael Stanton Korenfeld, Wildwood, MO (US)

(73) Assignee: DEL, LLC, Saint Louis, MO (US)

( * ) Notice: Subject to any disclaimer, the term of this patent is extended or adjusted under 35 U.S.C. 154(b) by 551 days.

(21) Appl. No.: 16/828,721

(22) Filed: Mar. 24, 2020

(65) Prior Publication Data
US 2021/0298952 A1 Sep. 30, 2021

(51) Int. Cl.
*A61F 9/007* (2006.01)
*A61F 2/10* (2006.01)
(Continued)

(52) U.S. Cl.
CPC ............ *A61F 9/00718* (2013.01); *A61F 2/10* (2013.01); *A61M 35/003* (2013.01); *A61B 2017/00424* (2013.01); *A61B 2017/00951* (2013.01); *A61F 2250/0064* (2013.01); *A61M 2210/0612* (2013.01)

(58) Field of Classification Search
CPC .................... A61F 9/00718; A61F 2/10; A61F 2250/0064; A61F 9/007; A61M 35/003; A61M 2210/0612; A61B 2017/00424; A61B 2017/00951; A41G 5/02; A41G 5/0086; A41G 5/0053; A41G 5/0073; A41G 5/008; A41G 5/00; A45D 2/48;
(Continued)

(56) References Cited

U.S. PATENT DOCUMENTS 3,590,828 A 7/1971 Prewitt
3,789,856 A 2/1974 Bomba
(Continued)

FOREIGN PATENT DOCUMENTS

AU 2015201939 11/2016
CN 204670589 9/2015
(Continued)

OTHER PUBLICATIONS

Chen, "Bearded Needle and Hook Tweezers", 2020, Machine Translation from Espacenet (Year: 2020).*
(Continued)

*Primary Examiner* — Kai H Weng
*Assistant Examiner* — Brandon W. Levy
(74) *Attorney, Agent, or Firm* — FIG. 1 Patents

(57) ABSTRACT

An instrument for isolating candidate eyelashes to attach prostheses includes an instrument tip which has a tip aperture. A candidate eyelash is disposed in a distal slot of the tip aperture. The instrument tip is advanced relative to the candidate eyelash and the instrument tip applies a force to eyelashes that are adjacent to the candidate eyelash. The application of the force actuates the eyelashes that are adjacent to the candidate eyelash away from the candidate eyelash. The candidate eyelash is actuated into an open area of the tip aperture and a prosthesis is attached to the candidate eyelash.

20 Claims, 13 Drawing Sheets

(51) Int. Cl.
*A61M 35/00* (2006.01)
*A61B 17/00* (2006.01)

(58) Field of Classification Search
CPC .............. A45D 44/00; A45D 2200/25; A45D 2040/0006; A45D 40/30; A45C 11/008
See application file for complete search history.

(56) References Cited

U.S. PATENT DOCUMENTS

| | | | |
|---|---|---|---|
| D576,352 S | 9/2008 | Brestoni | |
| 8,424,542 B1 | 4/2013 | Han | |
| 8,701,685 B2 | 4/2014 | Chipman | |
| 8,881,744 B2 | 11/2014 | McKinstry | |
| 8,925,558 B2 | 1/2015 | Johnson | |
| D758,009 S | 5/2016 | Berkos | |
| D788,985 S | 6/2017 | Hansen | |
| 2005/0091727 A1 | 5/2005 | Fowler | |
| 2007/0227550 A1* | 10/2007 | Merszei | A41G 5/02 132/53 |
| 2013/0042884 A1 | 2/2013 | Wilkinson | |
| 2013/0133681 A1* | 5/2013 | Chipman | A45D 44/00 132/286 |
| 2013/0152960 A1* | 6/2013 | Pays | A41G 5/02 132/216 |
| 2014/0135914 A1 | 5/2014 | Conant | |
| 2014/0178118 A1 | 6/2014 | Wu et al. | |
| 2014/0331383 A1 | 11/2014 | Bially | |
| 2015/0173442 A1 | 6/2015 | Raouf | |
| 2016/0219959 A1 | 8/2016 | Chipman et al. | |
| 2016/0353861 A1 | 12/2016 | Carey | |
| 2017/0000204 A1 | 1/2017 | Wibowo | |
| 2017/0049172 A1 | 2/2017 | Ahn | |
| 2019/0117356 A1* | 4/2019 | Bärtschi | A46B 5/0095 |

FOREIGN PATENT DOCUMENTS

| | | | |
|---|---|---|---|
| CN | 205193856 | | 4/2016 |
| CN | 210696118 U | * | 6/2020 |
| JP | 2006297038 | | 11/2006 |
| JP | 2012224390 | | 11/2012 |
| JP | 2015081387 | | 4/2015 |
| JP | 2016211095 | | 12/2016 |
| JP | 6122634 | | 4/2017 |
| KR | 101475003 | | 12/2014 |
| KR | 200476330 | | 2/2015 |
| WO | WO-2015031817 | | 3/2015 |

OTHER PUBLICATIONS

Amador, "Eyelashes divert airflow to protect the eye", Mar. 2015, 12 pages.
Dartt, "Complexity of the tear film: Importance in homeostasis and dysfunction during disease", Dec. 2013, 6 pages.
Glaser, "Epidemiologic Analysis of Change in Eyelash Characteristics With Increasing Age in a Population of Healthy Women", Nov. 2014, pp. 1208-1213.

* cited by examiner

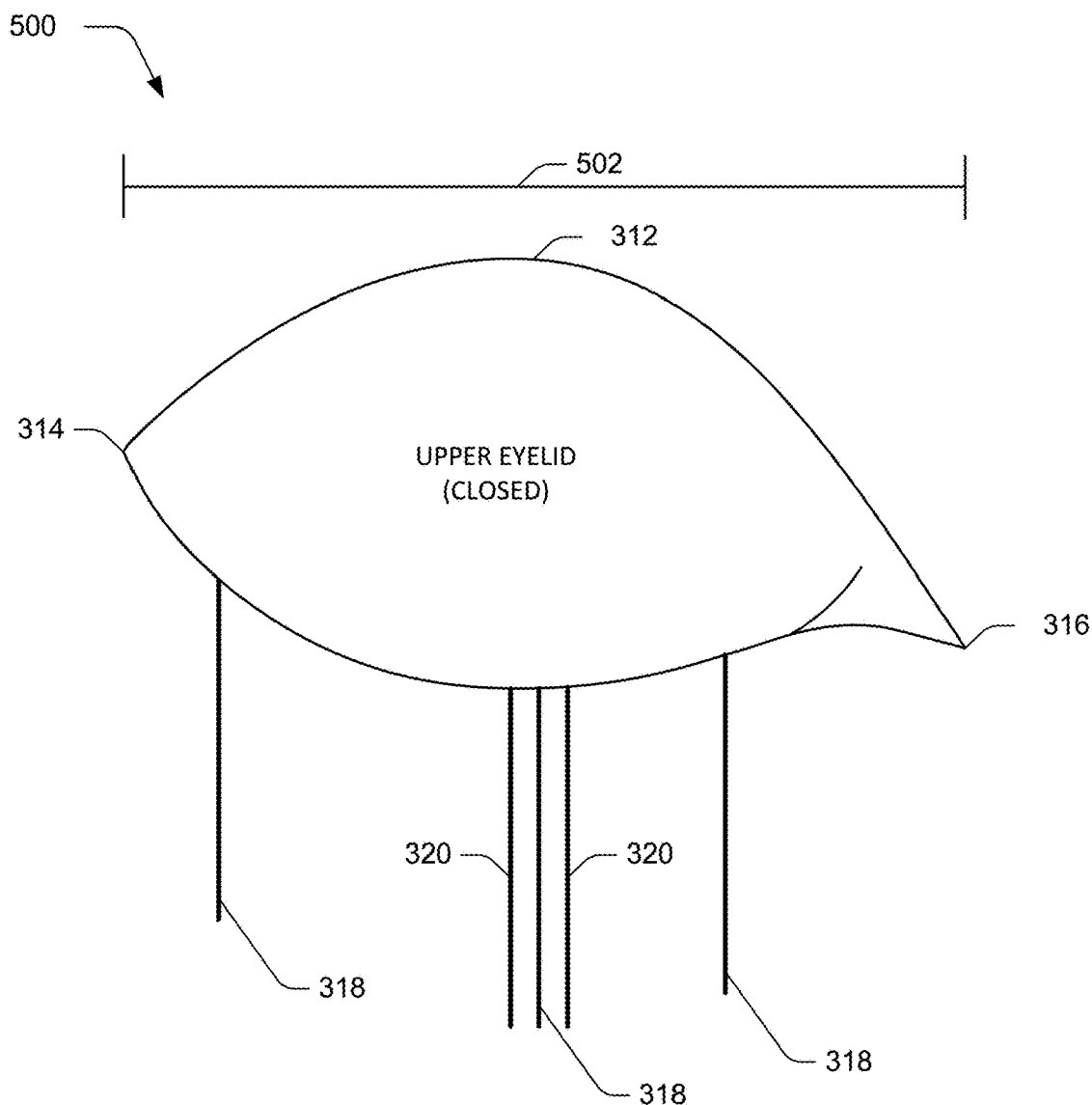
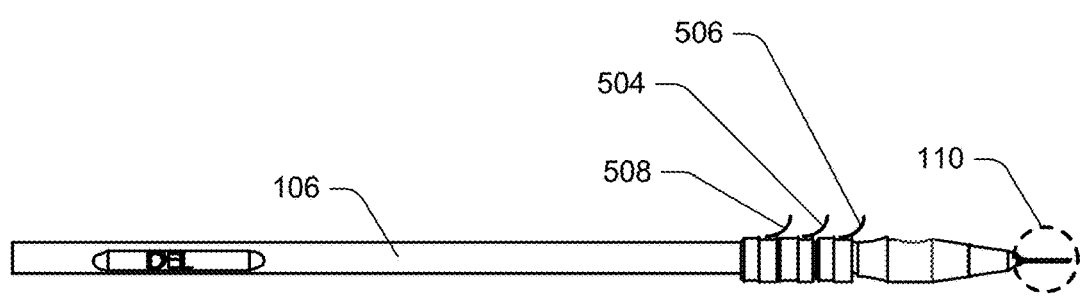
Fig. 5

INSTRUMENT FOR ISOLATING CANDIDATE EYELASHES TO ATTACH PROSTHESES

BACKGROUND

Dry eye syndrome or keratoconjunctivitis sicca is a condition that manifests itself as an insufficiency of tear film. The tear film is a multi-layer fluid that covers and protects the outer surface of the human eye. These multiple layers include a thin lipid layer and an aqueous/mucin region which increases in mucin concentration closest to the cornea. The lipid layer includes both polar and non-polar lipids and prevents evaporation of the underlying aqueous/mucin region which forms the majority of the tear film.

The insufficiency of the tear film that is associated with dry eye syndrome may be due to a lack of adequate tear production or excessive tear evaporation. There are many potential causes of this insufficiency. For example, dry eye has been associated with certain medications, other medical conditions, environmental conditions, and blinking less frequently such as during long periods of concentration. Increased age is a metric associated with an increased risk of dry eye syndrome. Other metrics identified as increasing risk of dry eye include having a diet low in vitamin A, wearing contact lenses, and being female.

It has been hypothesized that mammalian eyelash length may be tangentially related to an increased risk for dry eye syndrome in some mammals such as mammal species native to dusty, arid environments. Amador G. J. et al. evaluated images depicting the open eyes of 22 species of mammals in *Eyelashes divert airflow to protect the eye*, J. R. Soc. Interface 12:20141294 (2015). Based on these images, Amador G. J. et al. suggested that a ratio of eyelash length to width of the mammalian eye of 0.35±0.15 is optimal for open eyes of mammals in walking locomotion having a walking gait. Amador G. J. et al. also evaluated four species of birds which have been observed to have eye-lining feathers similar to mammalian eyelashes. For these species of birds, an ideal ratio of feather length to width of the bird eye of 0.86 was observed.

Persons suffering from dry eye syndrome experience discomfort including pain and burning of the eyes. Additional complications from dry eye can include corneal surface abrasions, corneal ulcers, and decreased visual acuity (loss of vision). Due to the severity of these potential complications, management of the syndrome is of critical importance as soon as keratoconjunctivitis sicca is diagnosed.

Conventional techniques for management of dry eye syndrome include over-the-counter eye drops, prescription medications, punctal plugs, and surgical procedures. Over-the-counter eye drops are the most common form of dry eye management. These drops are designed to temporarily replace tear film with artificial tears. Compared to over-the-counter eye drops, prescription medications are generally more effective for management of dry eye syndrome. The prescription medications currently available are delivered as eye drops and are designed to increase tear production.

Punctal plugs and surgical procedures are less common conventional approaches as treatment for dry eye. Punctal plugs seal tear ducts and prevent the tear film from draining into the tear ducts. A surgical procedure such as a tarsorrhaphy which narrows the eyelid opening may be performed in some cases to help prevent evaporation of the tear film.

There are no existing processes or procedures for screening humans for dry eye syndrome. Instead, this disorder is identified based on the presence of its symptoms. Once identified, dry eye can be quantified using a variety of tests such as a survey, a Schirmer's test, a slit lamp test, a tear break up time test, a tear meniscus height test, etc. Despite the various conventional techniques for management of dry eye syndrome, the condition remains pervasive. This may be partially due to an increasing average life expectancy for humans worldwide coupled with an increased risk of suffering from dry eye associated with increased age.

SUMMARY

Systems and techniques are described for instruments which isolate candidate eyelashes to attach prostheses. In one example, an instrument includes a handle, a prostheses repository, an adhesive reservoir, and an instrument tip. The instrument tip has a rigid outer perimeter and a tip aperture within the rigid outer perimeter. The tip aperture includes a distal slot configured to receive a candidate eyelash which is actuated into the distal slot by manipulation of the handle.

The instrument tip is advanced relative to the candidate eyelash which causes the instrument tip to apply a force to eyelashes adjacent to the candidate eyelash. This force actuates the adjacent eyelashes away from the candidate eyelash which is actuated into an open area of the tip aperture. A prosthesis is removed from the prostheses repository (e.g., using a forceps) and a portion of the prosthesis is immersed in an adhesive which may be housed in the adhesive reservoir. The prosthesis is then attached to the candidate eyelash.

The attached prosthesis introduces turbulence to airflow near an eye having the candidate eyelash. In one example, the prosthesis has a prosthesis length configured to introduce the turbulence to the airflow. This turbulence prevents the airflow from evaporating a tear film of the eye. In this way, dry eye syndrome is managed safely and effectively.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures. Entities represented in the figures may be indicative of one or more entities and thus reference may be made interchangeably to single or plural forms of the entities in the discussion.

FIGS. 3A, 3B, 3C, 3D, 3E, and 3F are illustrations of example representations of isolation of a candidate eyelash using an instrument tip.

FIG. 5 is an illustration of an example representation of management of dry eye syndrome using a first prosthesis having an ideal eyelash length, a second prosthesis having a length less than the ideal eyelash length, and a third prosthesis having a length greater than the ideal eyelash length.

DETAILED DESCRIPTION

Overview

Figure 1A:
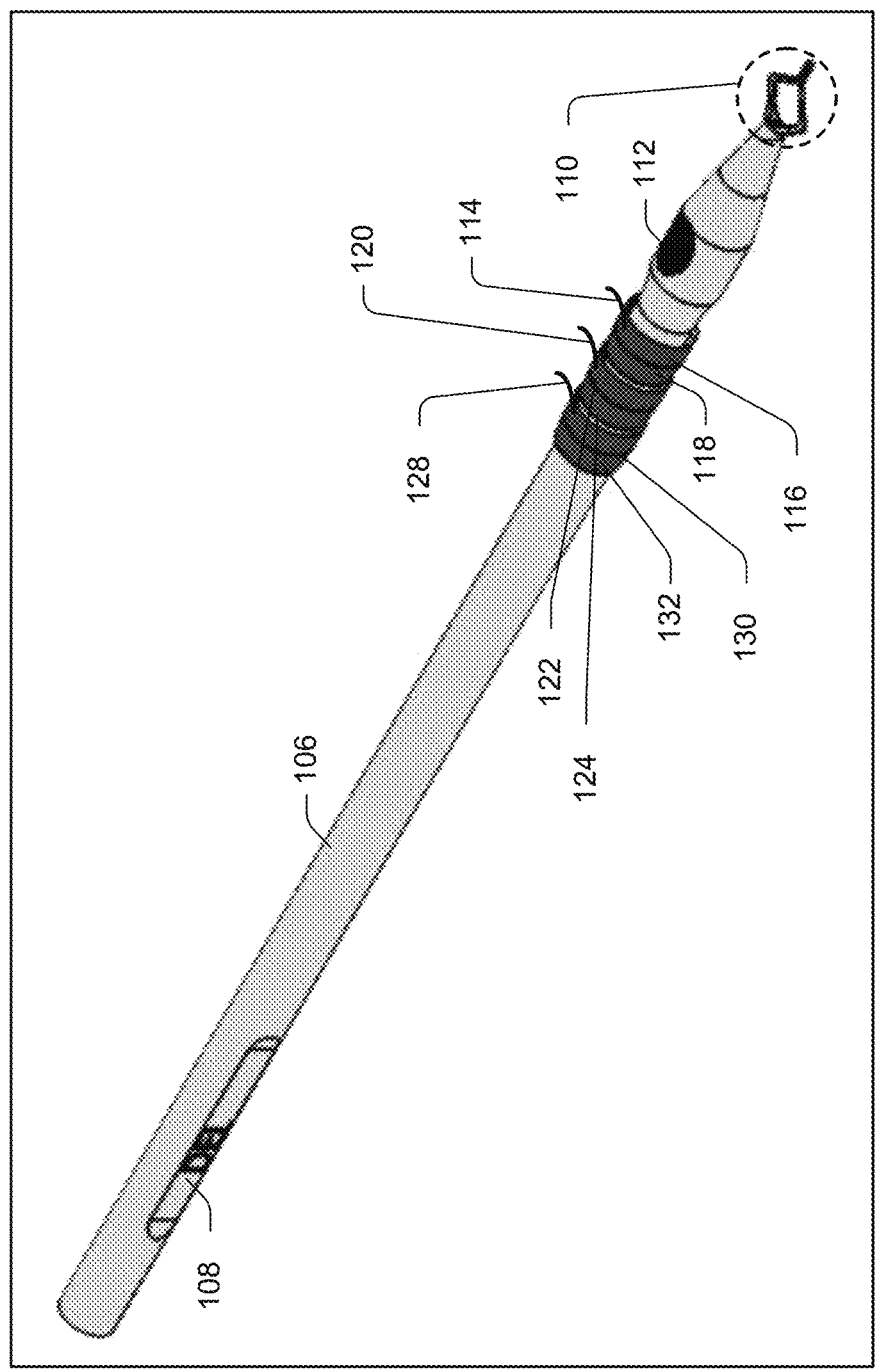
FIGS. 1A, 1B, and 1C are illustrations of example representations of an instrument for isolating candidate eyelashes to attach prostheses.

Dry eye syndrome adversely affects the lives of hundreds of millions of people globally which includes an estimated 15-25 million people in the US. The most widely used technique for treatment of dry eye in the US based on revenue is a prescription eye drop (cyclosporine ophthalmic emulsion 0.05%; Restasis) which increases tear production in about 15 percent of patients studied clinically. The same clinical study found that around 5 percent of patients given a placebo also increased tear production. Accordingly, conventional systems and techniques for managing dry eye syndrome are only marginally effective relative to placebos. Moreover, side effects of these conventional prescription eye drops include eye discomfort as well as itching and temporarily blurred vision.

Systems and techniques are described for instruments which isolate candidate eyelashes to attach prostheses to the candidate eyelashes. The prostheses are attached to the candidate eyelashes for management of dry eye syndrome in techniques which demonstrate significant improvements in efficacy relative to conventional techniques for managing dry eye. In one example, an instrument includes a handle, a prostheses repository, an adhesive reservoir, and an instrument tip.

For example, the instrument tip has a rigid outer perimeter and a tip aperture within the rigid outer perimeter. The tip aperture includes a distal slot and an open area proximal to the distal slot. In an example, a closed eyelid of an eye may have a candidate eyelash for attachment of a prosthesis as well as additional eyelashes that are adjacent to the candidate eyelash. These adjacent eyelashes can obstruct an attachment of the prosthesis to the candidate eyelash and the instrument tip is configured to isolate the candidate eyelash from the adjacent eyelashes to prevent such an obstruction.

For example, the distal slot is configured to receive the candidate eyelash which may be actuated into the distal slot by manipulation of the handle. In one example, the handle is manipulated to align the distal slot with the candidate eyelash, and the instrument tip is advanced relative to the candidate eyelash such that the candidate eyelash is actuated into the distal slot. As the instrument tip is advanced relative to the candidate eyelash, a portion of the rigid outer perimeter may apply a force to the eyelashes that are adjacent to the candidate eyelash.

This force actuates the adjacent eyelashes away from the candidate eyelash and the candidate eyelash is temporarily isolated from the adjacent eyelashes. For example, a geometry of the instrument tip is configured to deflect the adjacent eyelashes away from the candidate eyelash as the instrument tip is advanced relative to the candidate eyelash. As the adjacent eyelashes are deflected by the instrument tip, the candidate eyelash is actuated into the open area of the tip aperture.

A prosthesis can be removed from the prostheses repository (e.g., using a forceps) for attachment to the candidate eyelash. In one example, the prosthesis may be temporarily fixed to a prosthesis strip of the prostheses repository. This prosthesis strip may be disposed over a lateral projection of the instrument which orients the prosthesis at a lateral angle relative to a central axis of the handle.

In one example, the orientation of the prosthesis at the lateral angle pre-positions the prosthesis for attachment to the candidate eyelash which reduces procedural time needed to attach prostheses to candidate eyelashes. In another example, the orientation of the prosthesis at the lateral angle provides a user of the instrument with a direct line of sight from the prosthesis to the instrument tip and the isolated candidate eyelash. This direct line of sight may be under magnification and it enables the user of the instrument to quickly and accurately attach the prosthesis to the candidate eyelash.

After the prosthesis is removed from the prosthesis repository, a portion of the prosthesis is immersed in an adhesive in one example. This adhesive may be housed in the adhesive reservoir of the instrument. For example, the adhesive reservoir is disposed between the prostheses repository and the instrument tip. In this example, the adhesive reservoir is also included in the user's direct line of sight. In an example, the user removes the prosthesis, immerses the portion of the prosthesis in the adhesive, and attaches the prosthesis to the candidate eyelash in a single motion which the user can visualize even under magnification because of the user's direct line of sight.

After attaching the prosthesis to the candidate eyelash, the instrument tip can be retracted relative to the candidate eyelash which allows the adjacent eyelashes to return to a natural orientation. The attached prosthesis introduces turbulence to airflow near the eye having the candidate eyelash. For example, movements of the candidate eyelash are transferred to the prosthesis which causes a localized turbulence around the eye. In one example, the prosthesis has a prosthesis length configured to introduce the turbulence to the airflow. This turbulence prevents the airflow from evaporating a tear film of the eye. In this way, dry eye syndrome is managed safely and effectively.

The described techniques for treatment of dry eye syndrome have been evaluated relative to a prescription eye drop (lifitegrast ophthalmic solution 5%; Xiidra) as part of a Phase 2 Randomized Clinical Trial. Xiidra is FDA approved for treatment of dry eye syndrome. The Clinical Trial included 40 patients with 20 patients treated using the described systems and techniques and 20 patients treated using Xiidra as indicated.

In an interim analysis of the first 22 eyes randomized into the study, the described systems and techniques performed better than Xiidra when evaluated using best corrected visual acuity (BCVA), Hyperemia, fluorescent-antibody (FA) stain, and Lissamine green stain. Vision improvement is considered the best indicator of global effect on dry eyes. BVCA improved 91 percent for patients treated using Xiidra as indicated. BVCA improved 151 percent for patients treated using the described systems and techniques.

In the following discussion, an example environment is first described that may employ the techniques described herein. Example procedures are also described which may be performed in the example environment as well as other environments. Consequently, performance of the example procedures is not limited to the example environment and the example environment is not limited to performance of the example procedures.

Example Instrument

Figure 1B:
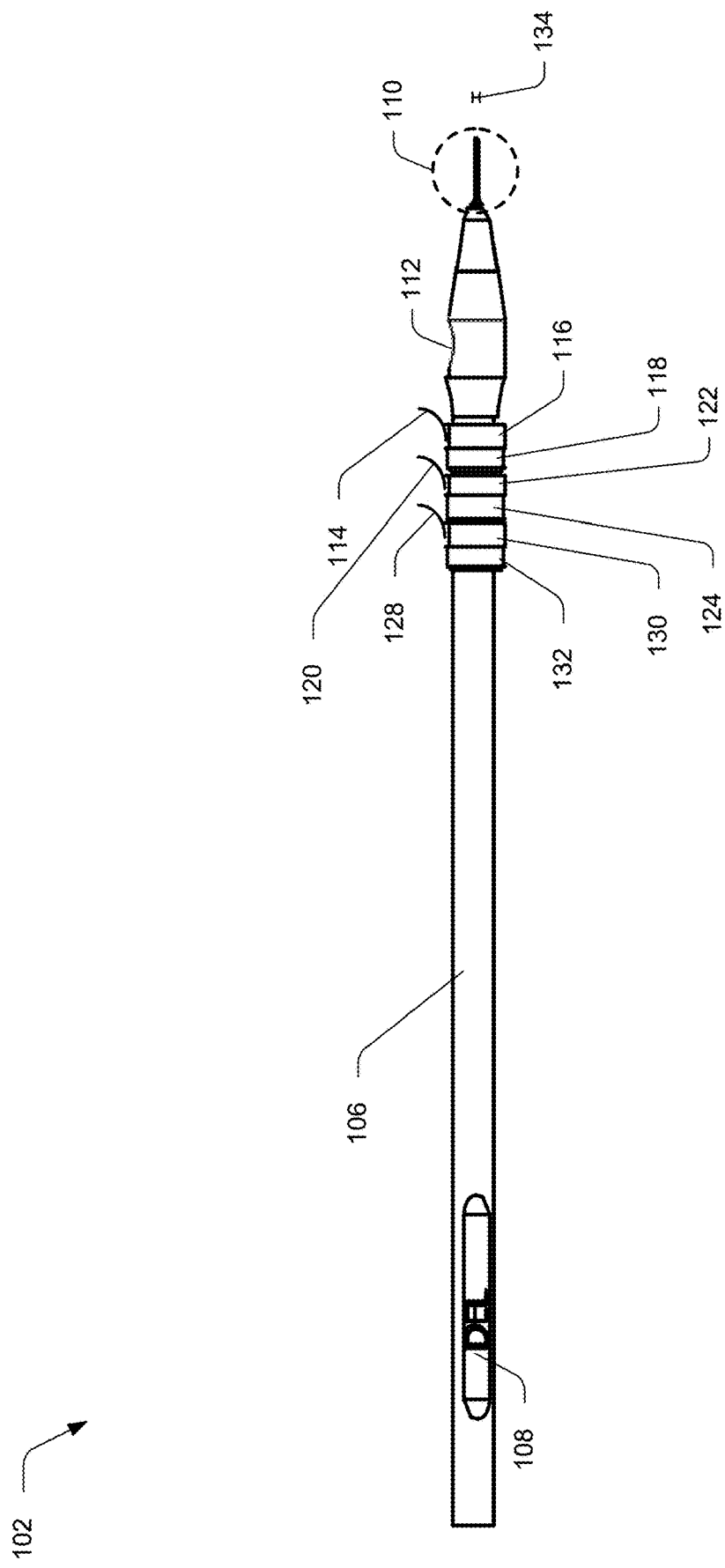
Figure 1C:
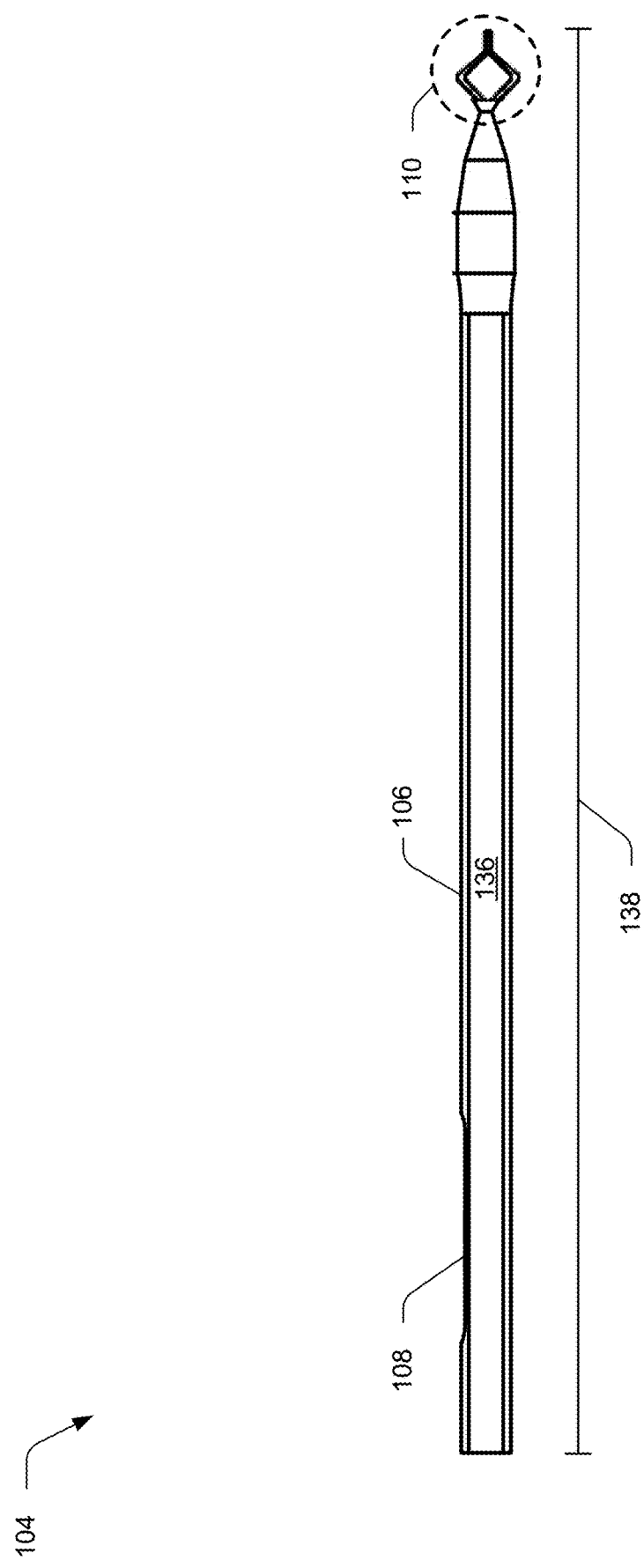

FIGS. 1A, 1B, and 1C are illustrations of example representations of an instrument for isolating candidate eyelashes to attach prostheses. FIG. 1A illustrates an example representation 100 of an isometric view of the instrument. FIG. 1B illustrates an example representation 102 of a side view of the instrument. FIG. 1C illustrates an example representation 104 of a bottom view of the instrument. As shown in FIG. 1A, the representation 100 includes a handle 106 which is illustrated to include a label 108. For example, the label 108 can include information about features of the instrument such as dimensional features.

The representation 100 also includes an instrument tip 110 and an adhesive reservoir 112. The adhesive reservoir 112 is configured to house an adhesive such as glue, cement, mucilage, paste, etc. As shown, the adhesive reservoir 112 is disposed in close proximity to the instrument tip 110. For example, a distance between the adhesive reservoir 112 and the instrument tip 110 may be configured such that a user of the instrument can simultaneously visualize both the adhesive reservoir 112 and the instrument tip 110 under magnification. In some examples, the distance between the adhesive reservoir 112 and the instrument tip 110 may be configured such that at least a portion of the adhesive reservoir 112 and at least a portion of the instrument tip 110 may be simultaneously visible under 5× magnification, 10× magnification, 15× magnification, 20× magnification, etc.

The adhesive reservoir 112 is illustrated as having dimensions configured to house an adhesive such that the adhesive is both easily accessible but also confined to the adhesive reservoir 112. For example, the adhesive reservoir 112 may have a length in a range of 3.0 to 8.0 millimeters, e.g., the adhesive reservoir 112 may have a length of approximately 5.7 millimeters. In some examples, the adhesive reservoir 112 may have a length of less than 3.0 millimeters or greater than 8.0 millimeters.

As illustrated, the representation 100 includes a first prosthesis 114 which is temporarily fixed to a first prosthesis strip 116 of a prostheses repository. The prostheses repository includes at least the first prosthesis 114, and the prostheses repository is disposed between the handle 106 and the instrument tip 110 in this example. In the illustrated example, the first prosthesis strip 116 includes a single first prosthesis 114; however, in other examples the first prosthesis strip 116 includes multiple first prostheses 114. For example, the first prosthesis strip 116 can include a range of 10 to 120 first prostheses 114. In another example, the first prosthesis strip 116 may include less than 10 first prostheses 114 or more than 120 first prostheses 114.

The first prosthesis strip 116 is disposed over a first lateral projection 118 which orients the first prosthesis strip 116 and the first prosthesis 114 at a lateral angle relative to a central axis of the handle 106. This orientation enables improved visualization of the first prosthesis 114 (e.g., under magnification). For example, when the handle 106 is oriented at a working angle, the user of the instrument has a direct line of sight between the first prosthesis 114 and the instrument tip 110 which can be viewed under magnification. Thus, the orientation of the of the first prosthesis 114 at the lateral angle relative to the central axis of the handle 106 enables the user to simultaneously visualize at least a portion of the first prosthesis 114 and at least a portion of the instrument tip 110 under magnification. In this manner, the user can visualize the first prosthesis 114 and/or the instrument tip 110 without adjusting a magnification source such as a microscope, a magnifying lens, etc.

As shown in FIG. 1A, the representation 100 includes a second prosthesis 120 which is temporarily fixed to a second prosthesis strip 122. In the illustrated example, the second prosthesis strip 122 includes a single second prosthesis 120. In other examples, the second prosthesis strip 122 includes multiple second prostheses 120. For example, the second prosthesis strip 122 can include a range of 10 to 120 second prostheses 120. In another example, the second prosthesis strip 122 may include less than 10 second prostheses 120 or more than 120 second prostheses 120.

The second prosthesis strip 122 is disposed over a second lateral projection 124. This second lateral projection 124 orients the second prosthesis strip 122 and the second prosthesis 120 at a lateral angle relative to the central axis of the handle 106. The orientation of the second prosthesis 120 at the lateral angle relative to the central axis of the handle 106 may provide the user of the instrument with a direct line of sight between the second prosthesis 120 and the instrument tip 110. For example, the user of the instrument can simultaneously view at least a portion of the second prosthesis 120 and at least a portion of the instrument tip 110 under magnification. In one example, the user of the instrument has a direct line of sight between the second prosthesis 120, the first prosthesis 114, and the instrument tip 110 which can be viewed under magnification.

In the illustrated example, the representation 100 includes a third prosthesis 128 which is temporarily fixed to a third prosthesis strip 130. As shown, the third prosthesis strip 130 includes a single third prosthesis 128 in this example. In another example, the third prosthesis strip 130 includes multiple third prostheses 128. For example, the third prosthesis strip 130 can include a range of 10 to 120 third prostheses 128. In another example, the third prosthesis strip 130 may include less than 10 third prostheses 128 or more than 120 third prostheses 128.

The third prosthesis strip 130 is disposed over a third lateral projection 132. As shown, the third lateral projection 132 orients the third prosthesis strip 130 and the third prosthesis 128 at a lateral angle relative to the central axis of the handle 106. The orientation of the third prosthesis 128 at the lateral angle relative to the central axis of the handle 106 allows the user of the instrument to visualize the third prosthesis 128 when the handle 106 is oriented at a working angle. This also can provide the user with a direct line of sight between the third prosthesis 128 and the instrument tip 110, e.g., under 5× magnification, 10× magnification, 15× magnification, 20× magnification, etc. In one example, the user has a direct line of sight between the third prosthesis 128, the second prosthesis 120, and the first prosthesis 114. In another example, the user has a direct line of sight between the third prosthesis 128, the second prosthesis 120, the first prosthesis 114, and the instrument tip 110.

The first prosthesis 114, the second prosthesis 120, and the third prosthesis 128 can be identical in one example. For example, the first prosthesis 114, the second prosthesis 120, and the third prosthesis 128 can each have a same length. In another example, each of the prostheses 114, 120, 128 can have a different length. In this example, the first prosthesis 114 may have a first length, the second prosthesis 120 may have a second length, and the third prosthesis 128 may have a third length. In one example, the label 108 may indicate a length of the prostheses 114, 120, 128.

For example, the first prosthesis 114 may have a length of approximately 9.0 millimeters, the second prosthesis 120 may have a length of approximately 10.0 millimeters, and the third prosthesis 128 may have a length of approximately 11.0 millimeters. In another example, the first prosthesis 114 may have a length of approximately 10.0 millimeters, the second prosthesis 120 may have a length of approximately 11.0 millimeters, and the third prosthesis 128 may have a length of approximately 12.0 millimeters. In an additional example, the first prosthesis 114 may have a length of approximately 9.5 millimeters, the second prosthesis 120 may have a length of approximately 10.5 millimeters, and the third prosthesis 128 may have a length of approximately 11.5 millimeters.

Consider an example in which the first prosthesis 114 can be attached to a candidate eyelash by removing the first prosthesis 114 from the first prosthesis strip 116 (e.g., using a forceps such as a jewelers forceps) and applying an adhesive to a portion of the first prosthesis 114. For example, this adhesive may be housed in the adhesive reservoir 112 and the candidate eyelash may be isolated in a portion of the instrument tip 110. As illustrated, the adhesive reservoir 112 is disposed between the first prosthesis strip 116 and the instrument tip 110. Thus, first prosthesis 114 may be removed from the first prosthesis strip 116, a portion of the first prosthesis 114 can be immersed in an adhesive housed in the adhesive reservoir 112, and the first prosthesis 114 may be attached to a candidate eyelash isolated in a portion of the instrument tip 110 in a single motion.

In this way, the first prosthesis 114 can be quickly attached to the candidate eyelash. In an example, the first lateral projection 118 orients the first prosthesis 114 in an orientation for attaching the first prosthesis 114 to the candidate eyelash. For example, the first prosthesis 114 may be attached to the candidate eyelash under magnification and the user of the instrument can simultaneously visualize the first prosthesis 114 and the candidate eyelash under the magnification.

Consider another example in which the first prosthesis 114 is attached to a first candidate eyelash. In this example, a second candidate eyelash may then be isolated in a portion of the instrument tip 110, e.g., by a manipulation of the handle 106. The second prosthesis 120 can be removed from the second prosthesis strip 122 (e.g., using a forceps) and a portion of the second prosthesis 120 can be immersed in an adhesive housed in the adhesive reservoir 112. The second prosthesis 120 may then be attached to the second candidate eyelash. This may be performed in a single motion and under magnification in one example. For example, the second lateral projection 124 orients the second prosthesis 120 in an orientation for attaching the second prosthesis 120 to the second candidate eyelash.

Continuing the previous example, after attaching the second prosthesis 120 to the second candidate eyelash, the handle 106 can be manipulated and a third candidate eyelash may be isolated in a portion of the instrument tip 110. The third prosthesis 128 may be removed from the third prosthesis strip 130 and immersed in an adhesive, e.g., housed in the adhesive reservoir 112. In this manner, the third prosthesis 128 can be attached to the third candidate eyelash in a single motion. For example, the third lateral projection 132 orients the third prosthesis 128 in an orientation for attaching the third prosthesis 128 to the third candidate eyelash.

Although the representation 100 illustrates the first prosthesis strip 116, the second prosthesis strip 122, and the third prosthesis strip 130, it is to be understood that the instrument can include any number of prosthesis strips. For example, the instrument may include a single prosthesis strip, two prosthesis strips, three prosthesis strips, four prosthesis strips, five prosthesis strips, and so forth. Additionally, each prosthesis strip can include a single prosthesis or multiple prostheses.

Although described in an example illustrating the first prosthesis 114, the second prosthesis 120, and the third prosthesis 128, it is to be appreciated that the instrument can include any number of prostheses. These prostheses can have different lengths or each prosthesis of the prostheses can have a same length. For example, the instrument can include some prostheses having a first length, some prostheses having a second length, some prostheses having a third length, some prostheses having a fourth length, some prostheses having a fifth length, and so forth.

In one example, each prosthesis strip may have prostheses having a unique length, e.g., the first prosthesis strip 116 may have prostheses having a first length and the second prosthesis strip 122 may have prostheses having a second length. In another example, each prosthesis strip may not include prostheses having a unique length. In this example, the first prosthesis strip 116 may have prostheses having a particular length and the second prosthesis strip 122 may have prostheses having the particular length. For example, a prosthesis strip can have prostheses of different lengths. In this example, the first prosthesis strip 116 may have some prostheses having a first length and the first prosthesis strip 116 may also have some prostheses having a second length.

As shown in FIG. 1B, the representation 102 illustrates an instrument tip height 134. The instrument tip height 134 can be a distance in a range of 0.1 to 0.6 millimeters, e.g., the instrument tip height 134 may be a distance of approximately 0.3 millimeters. In other examples, the instrument tip height 134 may be a distance of less than 0.1 millimeters or greater than 0.6 millimeters. For example, the instrument tip height 134 may be configured such that the instrument tip 110 is rigid, e.g., rigid enough to manipulate an eyelash adjacent to a candidate eyelash.

As illustrated in FIG. 1C, the representation 104 includes a flat portion 136 of an outer surface of the instrument. This flat portion 136 is configured to prevent rotational movement of the instrument about a central axis of the handle 106, e.g., while the flat portion 136 is disposed over a flat surface. The flat portion 136 at least partially defines an asymmetric geometry with respect to a transverse plane of the handle 106. As shown, the flat portion 136 is disposed opposite of the adhesive reservoir 112 and the prostheses 114, 120, 128. For example, the flat portion 136 can be disposed over a flat surface such as a tabletop and flat portion 136 prevents rotational movement of the adhesive reservoir 112 and the prostheses 114, 120, 128.

As shown, the instrument includes an overall length 138 which can be a distance in a range of 120 to 160 millimeters. In one example, the overall length 138 may be a distance of approximately 144.4 millimeters. In other examples, the overall length 138 may be a distance of less than 120 millimeters or greater than 160 millimeters.

In some examples, one or more portions of the instrument can manufactured by additive manufacturing, e.g., one or more portions of the instrument may be manufactured by selective laser sintering, selective heat sintering, selective laser melting, electron-beam melting, direct metal laser sintering, electron beam freeform fabrication, stereolithography, digital light processing, fused deposition modeling, laminated object manufacturing, ultrasonic additive manufacturing, vat photopolymerization, material jetting, binder jetting, laser engineered net shaping, etc. For example, the instrument may be manufactured by a machining process, a forging process, a casting process, a molding process such as injection molding, a forming process, a coating process, a joining process, etc.

In some examples, the instrument may be manufactured from any suitable material, e.g., polymers, metals, metal alloys, etc., or from any combination of suitable materials. For example, the instrument may be manufactured from one or more materials suitable for sterilization by ethylene oxidize sterilization, gamma sterilization, etc. In an example, the instrument may be manufactured from spring steel, e.g., the instrument may be manufactured from a shape memory material. In some examples, the instrument may be manufactured from stainless steel, e.g., instrument and/or its components may be manufactured from Type 301 stainless steel, Type 302 stainless steel, Type 303 stainless steel, Type 304 stainless steel, Type 304L stainless steel, Type 304LN stainless steel, Type 310 stainless steel, Type 316 stainless steel, Type 316L stainless steel, Type 316Ti stainless steel, Type 321 stainless steel, Type 430 stainless steel, Type 440 stainless steel, Type 17-7 stainless steel, etc.

In one example, the instrument may be manufactured from nitinol. In another example, the instrument may be manufactured from aluminum, e.g., the instrument may be manufactured from an aluminum alloy. In other examples, the instrument may be manufactured from a 6061 aluminum alloy, a 6061-T4 aluminum alloy, a 6061-T6 aluminum alloy, a 6063 aluminum alloy, a 6063 aluminum alloy, etc. In further examples, the instrument may be manufactured from titanium, e.g., the instrument may be manufactured from a titanium alloy. For example, the instrument may be manufactured from a Grade 5 titanium alloy, a Grade 6 titanium alloy, a Grade 7 titanium alloy, a Grade 7H titanium alloy, a Grade 9 titanium alloy, a Grade 11 titanium alloy, a Grade 12 titanium alloy, a Grade 16 titanium alloy, a Grade 17 titanium alloy, a Grade 18 titanium alloy, etc. In further examples, the instrument can be manufactured from a polymer such as Nylon, Turcite, Torlon, polyether ether ketone (PEEK), etc.

Figure 2:
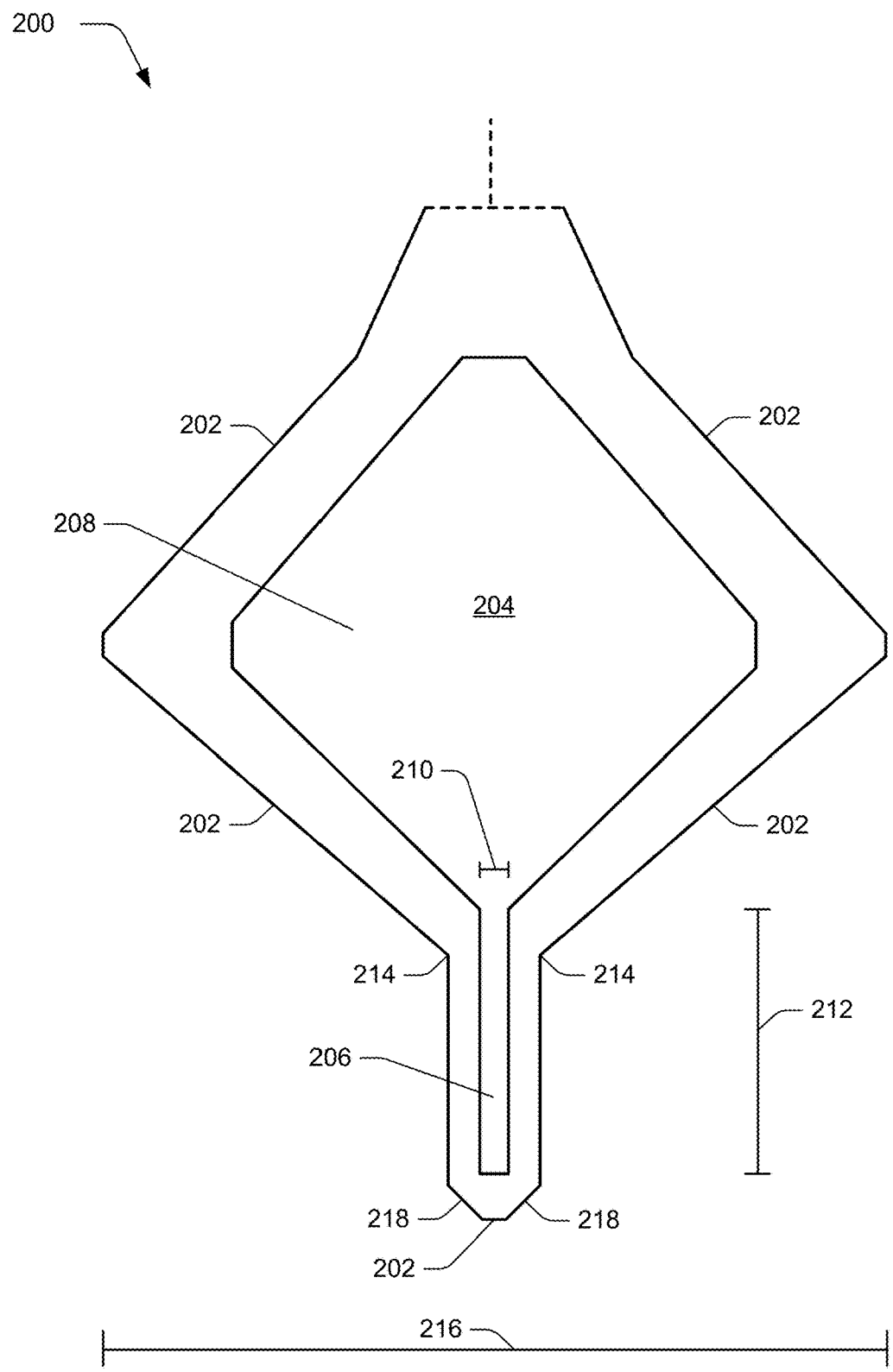
FIG. 2 is an illustration of an enlarged view of an instrument tip.

FIG. 2 is an illustration of an enlarged view 200 of an instrument tip 110. As shown in the enlarged view 200, the instrument tip 110 includes a rigid outer perimeter 202 and a tip aperture 204 disposed within the rigid outer perimeter 202. The tip aperture 204 includes a distal slot 210 and an open area 208 proximal to the distal slot 210. In the illustrated example, the open area 208 has a variable width although in some examples the open area 208 may have a fixed width.

The distal slot 206 includes a slot width 210 and a slot length 212. The slot width 210 is configured to receive a candidate eyelash. Thus, the slot width 210 can be a distance greater than an outer diameter of a candidate eyelash. For example, the slot width 210 may be a distance in a range of 0.1 to 0.3 millimeters. In one example, the slot width 210 may be a distance of approximately 0.2 millimeters. In other examples, the slot width 210 can be a distance of less than 0.1 millimeters or greater than 0.3 millimeters.

The slot length 212 may be a distance in a range of 1.7 to 2.5 millimeters, e.g., the slot length 212 may be a distance of approximately 2.1 millimeters. In some examples, the slot length 212 can be a distance of less than 1.7 millimeters or greater than 2.5 millimeters. For example, the slot length 212 may be a distance that is less than a length of a candidate eyelash.

As shown, the slot length 212 extends past eyelash deflectors 214 in this example. In another example, the slot length 212 may not extend past eyelash deflectors 214. The eyelash deflectors 214 are configured to deflect eyelashes adjacent to a candidate eyelash such that the candidate eyelash can be isolated in the tip aperture 204. In one example, the eyelash deflectors 214 are configured to deflect eyelashes adjacent to a candidate eyelash so that the candidate eyelash can be isolated in the open area 208.

As illustrated in the enlarged view 200, the instrument tip 110 includes a maximum outer diameter 216. The maximum outer diameter 216 is configured to provide an upper bound on an amount of deflection of the eyelashes adjacent to the candidate eyelash. For example, the maximum outer diameter 216 is a distance which deflects the adjacent eyelashes enough of a distance to isolate the candidate eyelash but not enough to damage the adjacent eyelashes. Consider an example in which the maximum outer diameter 216 is a distance less than two times the length of the adjacent eyelashes. In this example, the instrument tip 110 can deflect each adjacent eyelash a maximum distance of one half of the maximum outer diameter 216. Thus, in this example, the maximum outer diameter 216 prevents a deflection of the adjacent eyelashes which could damage the adjacent eyelashes.

In an example, the maximum outer diameter 216 may be a distance in a range of 3.0 to 9.0 millimeters. For example, the maximum outer diameter 216 may be a distance of approximately 6.7 millimeters. In this example, the maximum deflection distance of an eyelash adjacent to a candidate eyelash is approximately 3.35 millimeters. In other examples, the maximum outer dimeter 216 can be a distance of less than 3.0 millimeters or greater than 9.0 millimeters.

In some examples, the instrument tip 110 also includes distal deflectors 218. The distal deflectors 218 are configured to deflect eyelashes adjacent to a candidate eyelash even in scenarios in which the adjacent eyelashes are separated from the candidate eyelash by a distance less than a width of a portion of the instrument tip 110 that encloses the distal slot 206. In these scenarios, the adjacent eyelashes initially contact the distal deflectors 218 which deflect the adjacent eyelashes. These adjacent eyelashes are then further deflected by the eyelash deflectors 214.

Figure 3A:
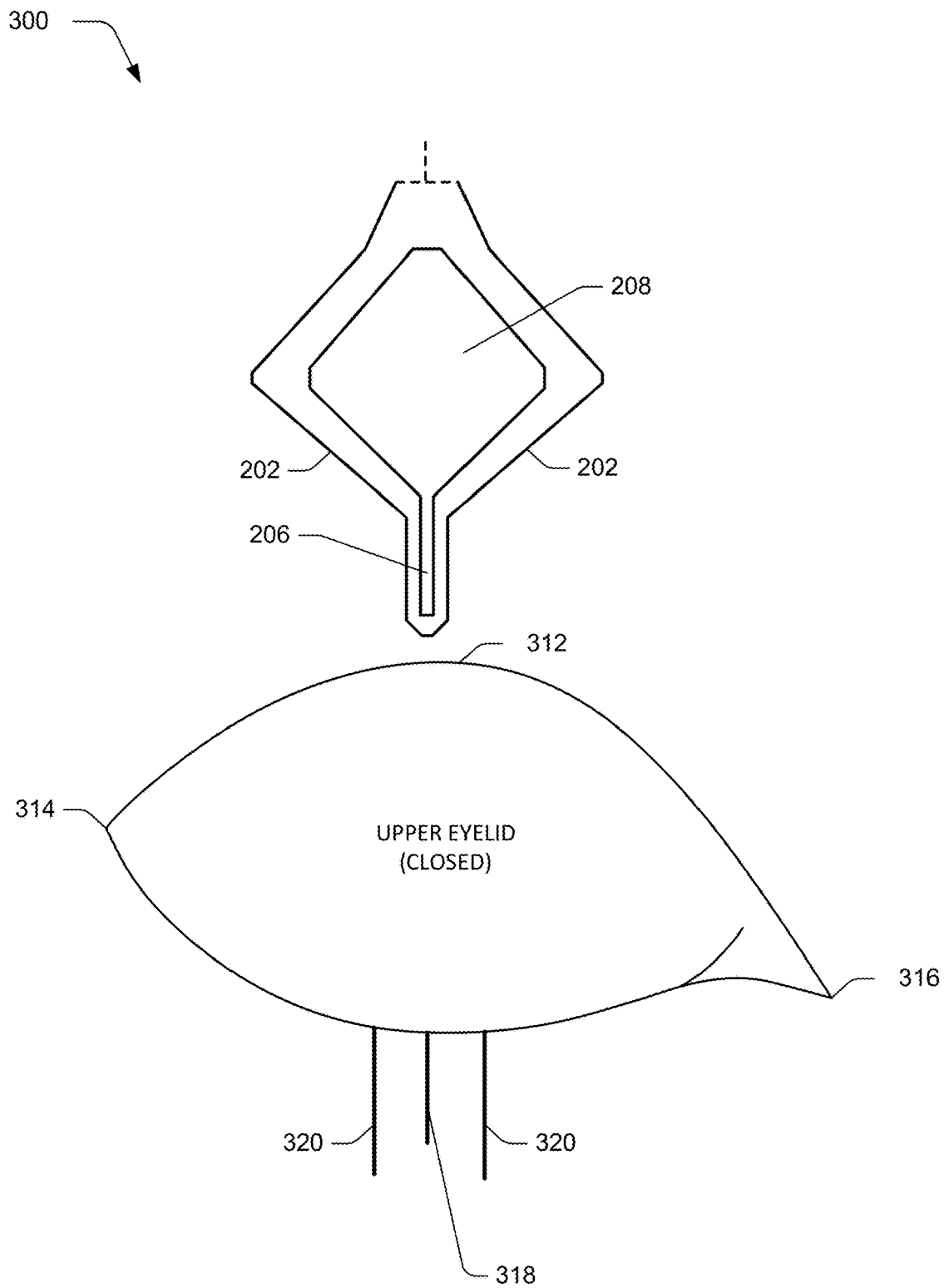
Figure 3B:
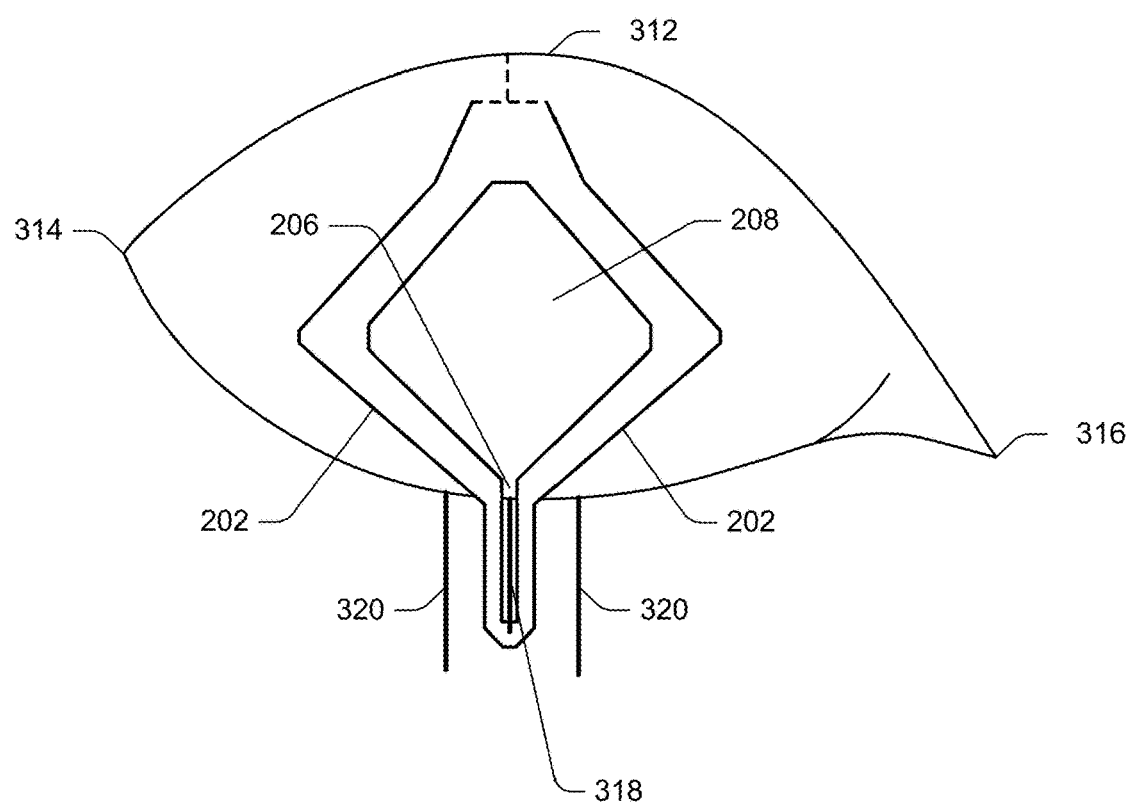
Figure 3C:
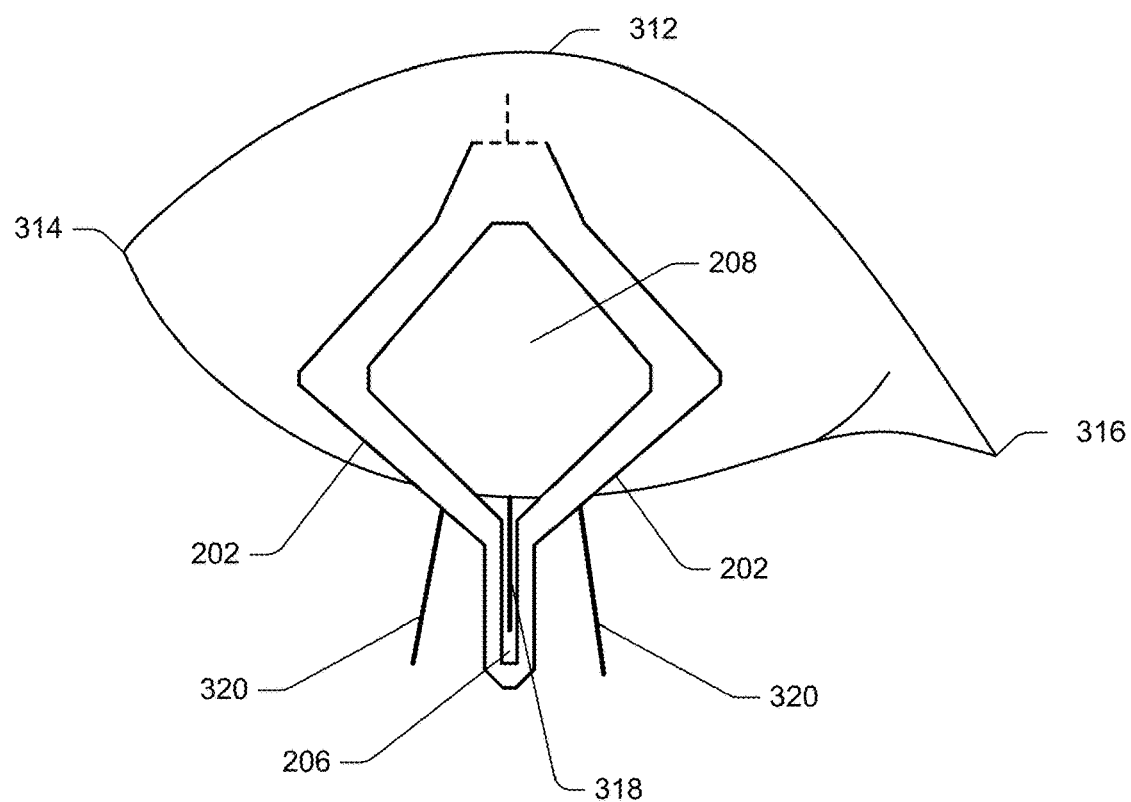
Figure 3D:
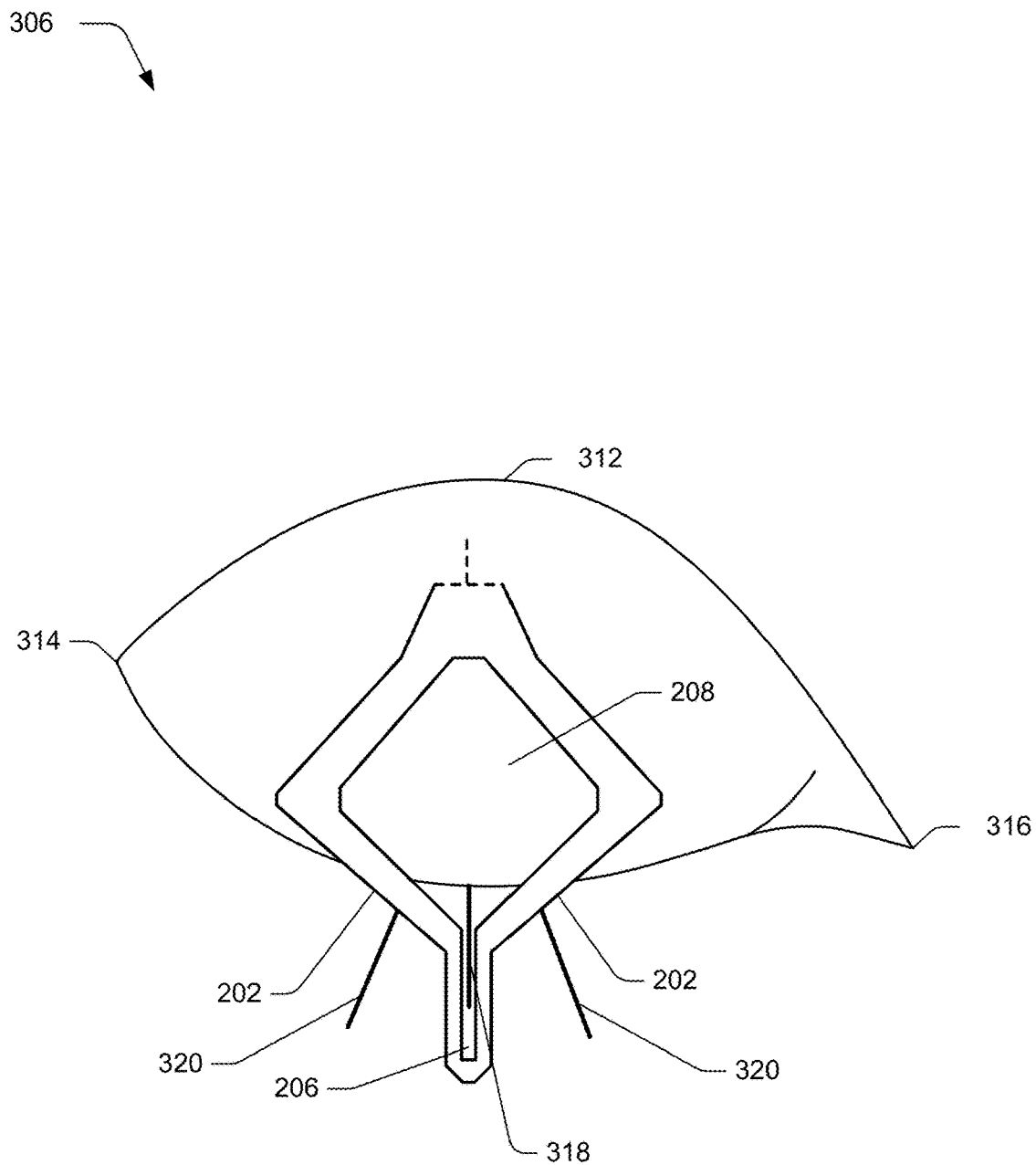
Figure 3E:
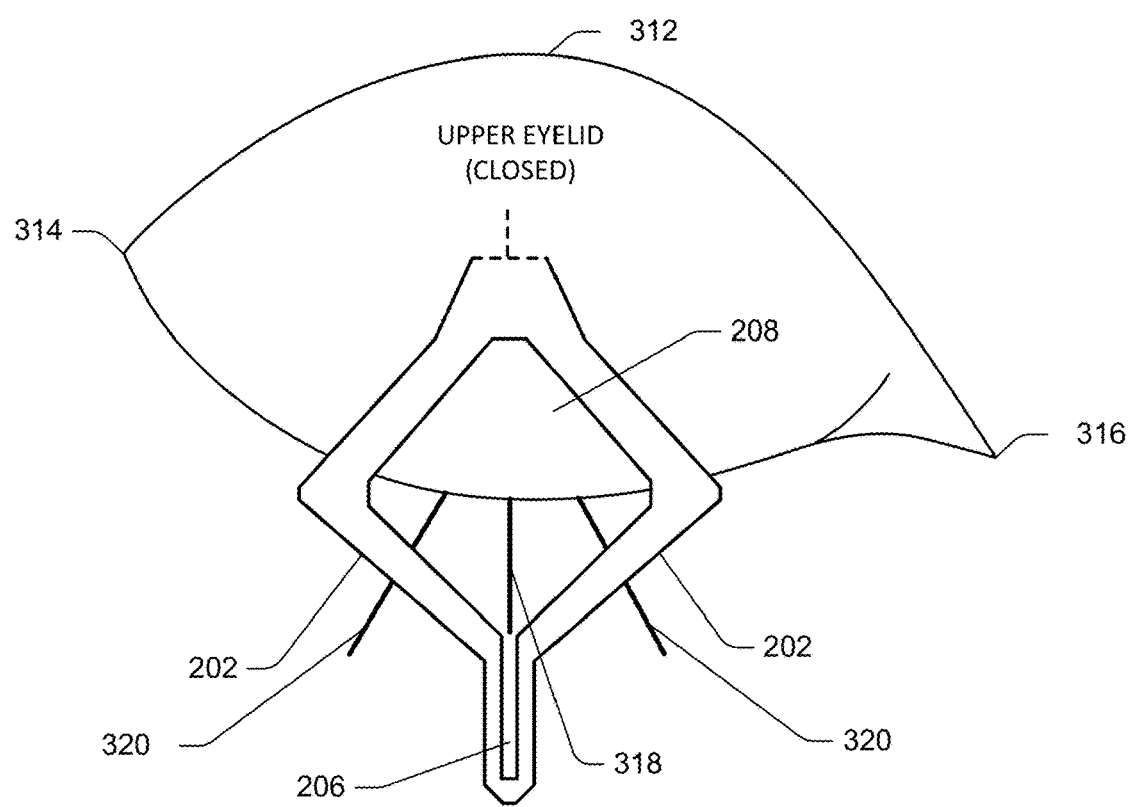
Figure 37:
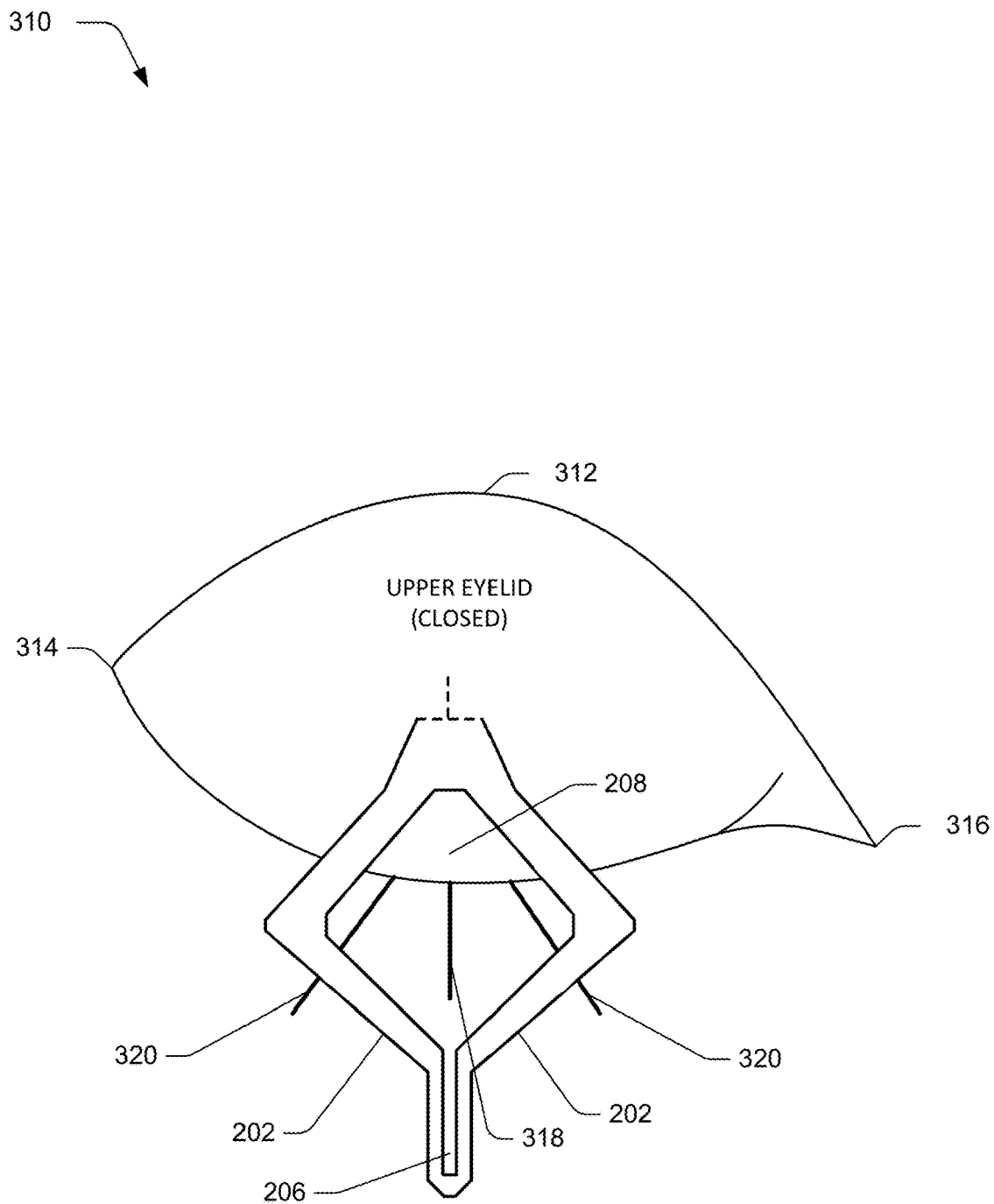

FIGS. 3A, 3B, 3C, 3D, 3E, and 3F are illustrations of example representations of isolation of a candidate eyelash using an instrument tip. FIG. 3A illustrates an example representation 300 of the candidate eyelash. FIG. 3B illustrates an example representation 302 of an actuation of the candidate eyelash into a distal slot 206 of an instrument tip 110. FIG. 3C illustrates an example representation 304 of an advancement of the instrument tip 110 relative to the candidate eyelash. FIG. 3D illustrates an example representation 306 of a force applied to eyelashes adjacent to the candidate eyelash. FIG. 3E illustrates an example representation 308 of a deflection of the eyelashes adjacent to the candidate eyelash. FIG. 3F illustrates an example representation 310 of an isolated candidate eyelash.

As shown in FIG. 3A, the representation 300 includes a right eye 312 having closed eyelids with a right upper eyelid shown. The right eye 312 includes a lateral canthus 314 and a medial canthus 316 and the right upper eyelid includes a candidate eyelash 318. The candidate eyelash 318 is illustrated as being disposed between adjacent eyelashes 320. The instrument tip 110 is manipulated, e.g., via the handle 106, to align the distal slot 206 with the candidate eyelash 318. Once aligned, the instrument tip 110 is advanced towards the candidate eyelash 318.

As illustrated in FIG. 3B, the candidate eyelash 318 is actuated into the distal slot 206 in the representation 302. For example, the instrument tip 110 is manipulated via the handle 106 to envelop the candidate eyelash 318 within the distal slot 206 and the instrument tip 110 is further manipulated down a length of the candidate eyelash 318 towards a base of the candidate eyelash 318 while the candidate eyelash is disposed in the distal slot 206. Actuating the candidate eyelash 318 into the distal slot 206 may be performed with or without use of a forceps (not shown).

As shown, the adjacent eyelashes 320 remain outside of the rigid outer perimeter 202 as the candidate eyelash 318 is actuated into the distal slot 206. In an example, the adjacent eyelashes 320 may initially contact the distal deflectors 218 which can deflect the adjacent eyelashes 320 as illustrated in the representation 302. In one example, actuating the candidate eyelash 318 into the distal slot 206 of the instrument tip 110 may be effective to isolate the candidate eyelash 318 from the adjacent eyelashes 320. For example, a portion of the rigid outer perimeter 202 can be used to apply a force to a superior portion of the candidate eyelash 318 which causes the candidate eyelash 318 to actuate such that the candidate eyelash 318 is inferior to a plane having the adjacent eyelashes 320.

As shown in FIG. 3C, the instrument tip 110 is advanced relative to the candidate eyelash 318 in the representation 304. In one example, the instrument tip 110 is advanced relative to the candidate eyelash 318 until the adjacent eyelashes 320 contact the eyelash deflectors 214 which are configured to deflect the adjacent eyelashes 320. For example, as the instrument tip 110 is advanced further relative to the candidate eyelash 318 the rigid outer perimeter 202 begins to deflect the adjacent eyelashes 320 away from the candidate eyelash 318. An example of such a deflection of the adjacent eyelashes 320 is depicted in the representation 306 presented in FIG. 3D. As shown in the representation 306, the instrument tip 110 is further advanced relative to the candidate eyelash 318 and the rigid outer perimeter 202 applies a force to the adjacent eyelashes 320. The application of this force actuates the adjacent eyelashes 320 away from the candidate eyelash 318 which is actuated into the open area 208.

As shown in FIG. 3E, the representation 308 illustrates a further deflection of the adjacent eyelashes 320. For example, the instrument tip 110 is advanced further relative to the candidate eyelash 318 which further deflects the adjacent eyelashes 320 relative to the candidate eyelash 318. As illustrated in FIG. 3F, the representation 310 illustrates an isolated candidate eyelash 318. The instrument tip 110 has been advanced relative to the candidate eyelash 318 such that the first prosthesis 114 can be attached to the candidate eyelash 318 without interference from the adjacent eyelashes 320.

In one example, the first prosthesis 114 can be attached to the candidate eyelash 318 by removing the first prosthesis 114 from the first prosthesis strip 116 (e.g., using a forceps such as a jewelers forceps) and applying an adhesive to a portion of the first prosthesis 114. This adhesive may be housed in the adhesive reservoir 112. For example, a portion of the first prosthesis 114 can be immersed in an adhesive housed in the adhesive reservoir 112, and the first prosthesis 114 may be attached to the candidate eyelash 318 which is isolated in the open area 208 of the instrument tip aperture 204. By isolating the candidate eyelash 318 in this way, the first prosthesis 114 can be attached to the candidate eyelash 318 without unintentionally attaching a portion of the first prosthesis 114 to the adjacent eyelashes 320. Once the first prosthesis 114 is attached to the candidate eyelash 318, an additional candidate eyelash can be isolated in a similar manner and the second prosthesis 120 may be attached to the additional candidate eyelash in one example.

In general, functionality, features, and concepts described in relation to the examples above and below may be employed in the context of the example procedures described in this section. Further, functionality, features, and concepts described in relation to different figures and examples in this document may be interchanged among one another and are not limited to implementation in the context of a particular figure or procedure. Moreover, blocks associated with different representative procedures and corresponding figures herein may be applied together and/or combined in different ways. Thus, individual functionality, features, and concepts described in relation to different example environments, devices, components, figures, and procedures herein may be used in any suitable combinations and are not limited to the particular combinations represented by the enumerated examples in this description.

Example Procedures

Figure 4:
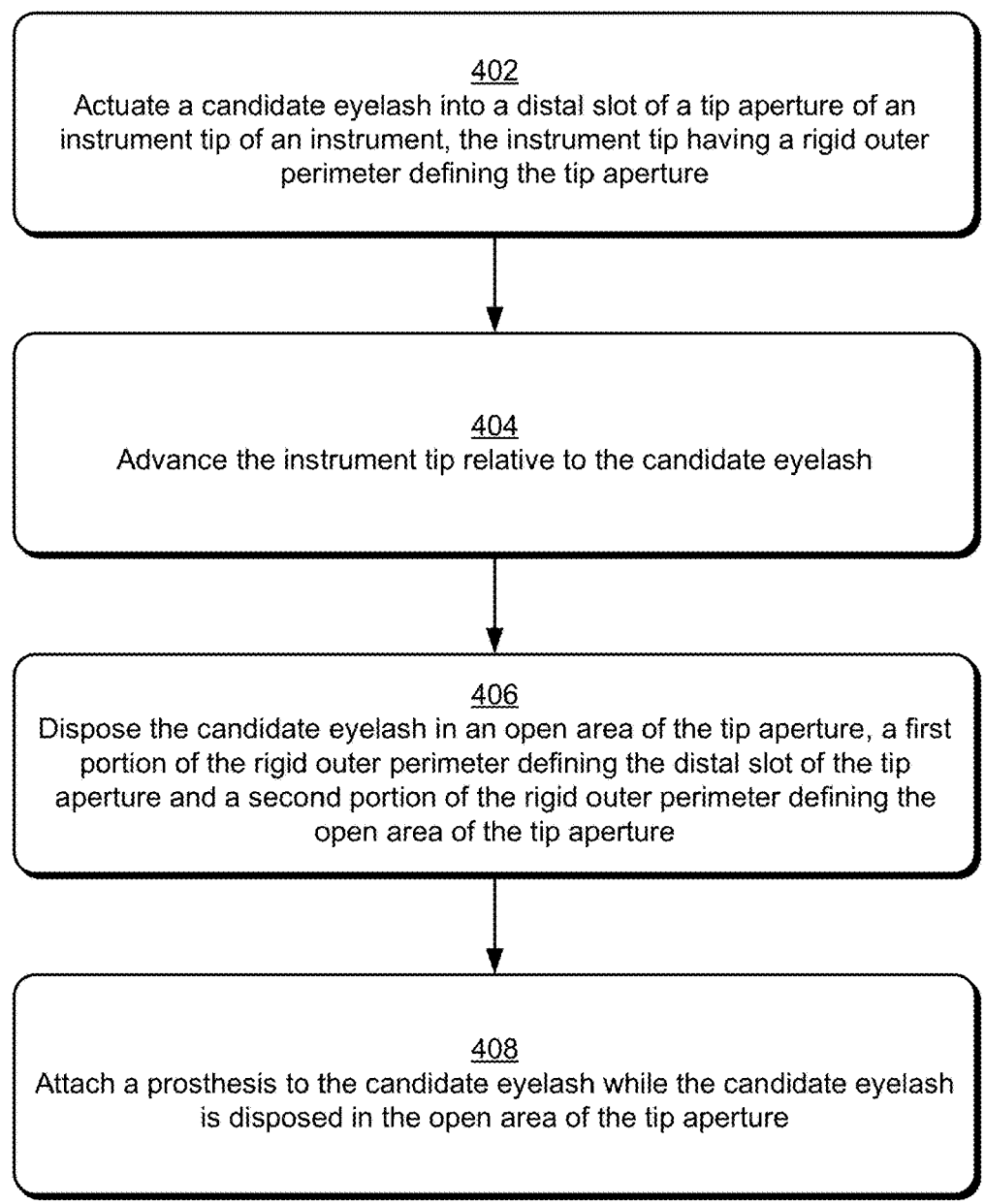
FIG. 4 is a flow diagram depicting a procedure in an example in which a candidate eyelash is disposed in an open area of a tip aperture of an instrument tip and a prosthesis is attached to the candidate eyelash while the candidate eyelash is disposed in the open area of the tip aperture.

The following discussion describes techniques that may be implemented utilizing the previously described systems and devices. The procedures are shown as a set of blocks that specify operations performed and are not necessarily limited to the orders shown for performing the operations by the respective blocks. In portions of the following discussion, reference may be made to FIGS. 1-3. FIG. 4 is a flow diagram depicting a procedure 400 in an example in which a candidate eyelash is disposed in an open area of a tip aperture of an instrument tip and a prosthesis is attached to the candidate eyelash while the candidate eyelash is disposed in the open area of the tip aperture.

A candidate eyelash is actuated into a distal slot of a tip aperture of an instrument tip of an instrument (block 402), the instrument tip having a rigid outer perimeter defining the tip aperture. For example, the handle 106 may be manipulated to actuate the candidate eyelash 318 into the distal slot 206 of the tip aperture 204 of the instrument tip 110. The instrument tip is advanced relative to the candidate eyelash (block 404). In one example, the handle 106 may be manipulated to advance the instrument tip 110 relative to the candidate eyelash 318.

The candidate eyelash is disposed in an open area of the tip aperture (block 406), a first portion of the rigid outer perimeter defining the distal slot of the tip aperture and a second portion of the rigid outer perimeter defining the open area of the tip aperture. For example, the handle 106 can be manipulated to dispose the candidate eyelash 318 in the in the open area 208 of the tip aperture 204. A prosthesis is attached to the candidate eyelash while the candidate eyelash is disposed in the open area of the tip aperture (block 408). In one example, the first prosthesis 114 may be attached to the candidate eyelash 318 while the candidate eyelash 318 is disposed in the open area 208 of the tip aperture 204. For example, the first prosthesis 114 may be removed from the first prosthesis strip 116 (e.g., using a forceps), and a portion of the first prosthesis 114 can be immersed in an adhesive housed in the adhesive reservoir 112. The first prosthesis 114 can then be attached to the candidate eyelash 318.

FIG. 5 is an illustration of an example representation 500 of management of dry eye syndrome using a first prosthesis having an ideal eyelash length, a second prosthesis having a length less than the ideal eyelash length, and a third prosthesis having a length greater than the ideal eyelash length. As shown, the representation 500 includes the right eye 312 having closed eyelids with a right upper eyelid shown. The upper eyelid includes multiple candidate eyelashes 318. A palpebral fissure width for the right eye 312 is determined as a distance 502 between the lateral canthus 314 and the medial canthus 316. The distance 502 can be determined using any suitable technique, e.g., the distance 502 may be measured using a pair of calipers, a ruler, a reticle, etc.

The distance 502 can be used to generate an ideal eyelash length. In one example, the ideal eyelash length may be expressed as:

$$L_{IDL} = D_{PFW} * \rho$$

where: $L_{IDL}$ is the ideal eyelash length; $D_{PFW}$ is the distance 502; and $\rho$ is a constant that is greater than zero.

For example, ρ is a constant between zero and one. In some examples, ρ may be a constant in a range of 0.20 to 0.45, e.g., ρ may be a constant of 0.33. In other examples, ρ may be a constant of less than 0.20 or greater than 0.45. A value of ρ may be determined heuristically, statistically, analytically, etc. In one example, the value of ρ is based on anatomical data that describes eyelash lengths of multiple mammalian species. In another example, the value of ρ is based on clinical data describing eyelash lengths of groups of patients having dry eye syndrome as well as groups of patients that do not have dry eye syndrome.

The representation 500 includes a prosthesis 504, a shorter prosthesis 506, and a longer prosthesis 508. In this example, the prosthesis 504 has a length equal to the ideal eyelash length based on the distance 502. For example, the shorter prosthesis 506 has a length less than the length of the prosthesis 504 and the longer prosthesis 508 has a length greater than the length of the prosthesis 504.

In some examples, the length of the shorter prosthesis 506 and the length of the longer prosthesis 508 are a function of the ideal eyelash length which may be expressed as:

$$L_{sp} = L_{IDL} - \delta$$

$$L_{lp} = L_{IDL} + \delta$$

where: $L_{sp}$ is a length of the shorter prosthesis 506; $L_{lp}$ is a length of the longer prosthesis 508; and δ is a length constant.

Consider an example in which the distance 502 is approximately 33.0 millimeters, the value of ρ is 0.33, and the value of δ is 1.0 millimeters. In this example, the prosthesis 504 has the ideal eyelash length of approximately 11.0 millimeters. For example, the shorter prosthesis 506 may have a length of approximately 10.0 millimeters and the longer prosthesis 508 may have a length of approximately 12.0 millimeters.

Consider an additional example in which the distance 502 is approximately 30.0 millimeters, the value of ρ is 0.33, and the value of δ is 1.0 millimeters. In this additional example, the prosthesis 504 has the ideal eyelash length of approximately 10.0 millimeters. Thus, the shorter prosthesis 506 may have a length of approximately 9.0 millimeters and the longer prosthesis 508 may have a length of approximately 11.0 millimeters.

Attaching the prosthesis 504, the shorter prosthesis 506, and the longer prosthesis 508 to the candidate eyelashes 318 introduces multiple turbulences to airflow around the right eye 312. For example, movements of the candidate eyelashes 318 cause movements of the prosthesis 504, the shorter prosthesis 506, and/or the longer prosthesis 508. The movements of the prosthesis 504, the shorter prosthesis 506, and/or the longer prosthesis 508 introduce the multiple turbulences to the airflow around the right eye 312. These multiple turbulences disrupt the airflow incident to the tear film of the right eye 312 which prevents the airflow from evaporating the tear film. Thus, the tear film is maintained and dry eye syndrome is effectively managed for the right eye 312.

Although the introduction of the multiple turbulences to the airflow around the right eye 312 is effective to prevent the tear film from evaporating, there may be some limits to the clinically beneficial effects of introduction of these turbulences to the airflow. This is because introduction of too much turbulence to the airflow around the right eye 312 can damage a lipid layer of the tear film. The lipid layer prevents an underlying aqueous/mucin region of the tear film from evaporating and as a result, damaging the lipid layer can facilitate evaporation of the tear film. For this reason, lengths of the prosthesis 504, the shorter prosthesis 506, and the longer prosthesis 508 introduce enough turbulence to the airflow incident to the tear film to prevent the tear film from evaporating but do not introduce turbulence sufficient to damage the lipid layer.

Figure 6:
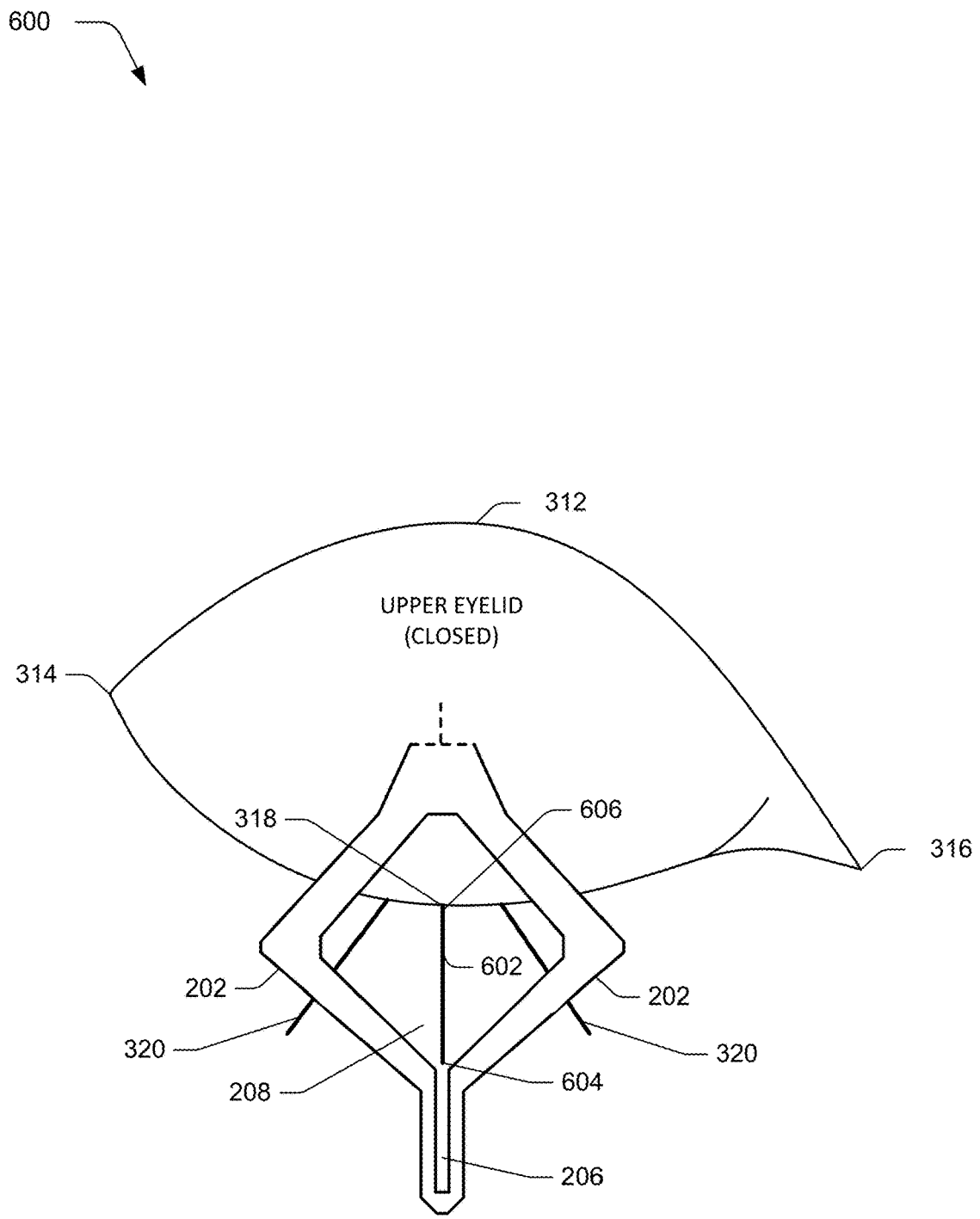
FIG. 6 is an illustration of an example representation of a prosthesis attached to an isolated candidate eyelash.

FIG. 6 is an illustration of an example representation 600 of a prosthesis attached to an isolated candidate eyelash. As shown, the representation 600 includes the right eye 312 and the instrument tip 110 is oriented such that the candidate eyelash 318 is isolated from the adjacent eyelashes 320. A prosthesis 602 is attached to the candidate eyelash 318, e.g., by an adhesive or any suitable attachment technique. The prosthesis 602 includes a prosthesis proximal end 604 and a prosthesis distal end 606.

In the illustrated example, the prosthesis 602 is attached to the candidate eyelash 318 such that the prosthesis distal end 606 is in close proximity to a distal end of an exposed portion of the candidate eyelash 318. In this example, the prosthesis 602 is attached to the candidate eyelash 318 in a manner in which the prosthesis distal end 606 is as close to the upper eyelid as possible without contacting the upper eyelid. In other examples, the prosthesis 602 may be directly attached to the upper eyelid, e.g., the prosthesis 602 can be surgically implanted in the upper eyelid.

As illustrated in FIG. 6, the prosthesis 602 is disposed over the candidate eyelash 318 wherein the prosthesis proximal end 604 extends past a proximal end of the candidate eyelash 318. Once the prosthesis 602 is attached to the candidate eyelash 318, the instrument tip 110 can be actuated (e.g., retracted relative to the candidate eyelash 318), and the adjacent eyelashes 320 gradually return to a natural orientation. Any movement of the candidate eyelash 318 such as an actuation of the candidate eyelash 318 is transferred to the prosthesis 602 which actuates the prosthesis 602. This actuation of the prosthesis 602 introduces turbulence to airflow near the right eye 312 which prevents the tear film from evaporating.

The prosthesis 602 also introduces turbulence to airflow near the right eye when the candidate eyelash 318 is static or not moving. For example, airflow in a region beyond the proximal end of the candidate eyelash 318 was uninhibited before attaching the prosthesis 602 to the candidate eyelash 318. Since the prosthesis proximal end 604 extends a distance beyond the proximal end of the candidate eyelash 318, a portion of the airflow which was previously uninhibited is now restricted by the prosthesis 602. This restriction also introduces turbulence to airflow near the right eye 312 which prevents the tear film from evaporating. In this way, dry eye syndrome is managed safely and effectively.

In some examples, a portion of the prosthesis 602 is curved such that the prosthesis proximal end 604 is disposed inferior to the prosthesis distal end 606 while the prosthesis 602 is attached to the candidate eyelash 318. In the examples in which a portion of the prosthesis 602 is curved, a curved portion of the prosthesis 602 that extends beyond the proximal end of the candidate eyelash 318 may further introduce turbulence to airflow near the right eye 312. This is because the curved portion increases a volume of the prosthesis 602 in a sagittal plane of the right eye 312 which further introduces turbulence to the airflow near the right eye 312.

Example Clinical Data

The described systems and techniques for treatment of dry eye syndrome by attaching the prosthesis 504, the shorter prosthesis 506, and the longer prosthesis 508 to the candidate eyelashes 318 have been evaluated relative to a prescription eye drop (lifitegrast ophthalmic solution 5%;

Xiidra) as part of a Phase 2 Randomized Clinical Trial. Xiidra is FDA approved for treatment of dry eye syndrome. The Clinical Trial included 40 patients with 20 patients treated using the described systems and techniques and 20 patients treated using Xiidra as indicated. Results of the Clinical Trial conclude that the described systems and techniques and Xiidra are similar in effectiveness in treatment of dry eye syndrome. The time to endpoint was three weeks for the described systems and techniques and the time to endpoint was five weeks for Xiidra. In an interim analysis of the first 22 eyes randomized into the study, the described systems and techniques performed better than Xiidra when evaluated using best corrected visual acuity (BCVA), Hyperemia, fluorescent-antibody (FA) stain, and Lissamine green stain. Vision improvement is considered the best indicator of global effect on dry eyes. BVCA improved 91 percent for patients treated using Xiidra as indicated. BVCA improved 151 percent for patients treated using the described systems and techniques. Thus, during an interim analysis visual acuity improved significantly more in patients treated using the described systems and techniques than in patients treated using Xiidra in the Clinical Trial.

CONCLUSION

Although aspects of an instrument for isolating candidate eyelashes to attach prostheses have been described in language specific to structural features and/or methods, it is to be understood that the appended claims are not necessarily limited to the specific features or methods described. Rather, the specific features and methods are disclosed as example implementations of an instrument for isolating candidate eyelashes to attach prostheses, and other equivalent features and methods are intended to be within the scope of the appended claims. Further, various different examples are described and it is to be appreciated that each described example can be implemented independently or in connection with one or more other described examples.

What is claimed is:

1. An instrument for isolating a candidate eyelash from adjacent eyelashes to attach a prosthesis to the candidate eyelash, the instrument comprising:
  a handle having an asymmetric geometry with respect to a transverse plane of the handle;
  an instrument tip having a rigid outer perimeter and a tip aperture within the rigid outer perimeter, the tip aperture including a distal slot having a slot width configured to receive the candidate eyelash;
  eyelash deflectors of the instrument tip configured to deflect the adjacent eyelashes away from the candidate eyelash as the instrument tip is advanced relative to the candidate eyelash, the distal slot having a slot length that extends past the eyelash deflectors;
  a maximum outer diameter of the instrument tip configured to provide an upper bound on an amount of deflection of the adjacent eyelashes; and
  a prostheses repository including at least one prosthesis, the prostheses repository disposed between the handle and the instrument tip.

2. The instrument as described in claim 1, further comprising an adhesive reservoir disposed between the instrument tip and the prostheses repository, the adhesive reservoir configured to house an adhesive.

3. The instrument as described in claim 1, further comprising a lateral projection of the prostheses repository configured to receive the at least one prosthesis and orient the at least one prosthesis at a lateral angle relative to a central axis of the handle.

4. The instrument as described in claim 3, further comprising a prosthesis strip disposed between the at least one prosthesis and the lateral projection, the prosthesis strip configured to temporarily fix the at least one prosthesis to the prosthesis strip.

5. The instrument as described in claim 4, wherein the prosthesis strip includes at least one additional prosthesis.

6. The instrument as described in claim 4, further comprising an additional prosthesis strip disposed between an additional lateral projection of the prostheses repository and an additional prosthesis, the additional prosthesis temporarily fixed to the additional prosthesis strip.

7. The instrument as described in claim 6, wherein the additional prosthesis has a length that is greater than a length of the at least one prosthesis.

8. The instrument as described in claim 6, wherein the additional prosthesis has a length that is less than a length of the at least one prosthesis.

9. The instrument as described in claim 1, further comprising a flat portion of an outer surface of the instrument at least partially defining the asymmetric geometry, the flat portion configured to prevent rotational movement of the instrument about a central axis of the handle while the flat portion is disposed over a flat surface.

10. The instrument as described in claim 1, wherein the rigid outer perimeter has a first portion that defines the distal slot of the tip aperture and a second portion that defines an open area of the tip aperture, the open area having a variable width.

11. A method for attaching a prosthesis to a candidate eyelash, the method comprising:
  deflecting eyelashes adjacent to the candidate eyelash by distal deflectors of an instrument tip of an instrument;
  actuating the candidate eyelash into a distal slot of a tip aperture of the instrument tip, the instrument tip having a rigid outer perimeter defining the tip aperture;
  advancing the instrument tip relative to the candidate eyelash;
  deflecting the eyelashes adjacent to the candidate eyelash by eyelash deflectors of the instrument tip;
  disposing the candidate eyelash in an open area of the tip aperture, a first portion of the rigid outer perimeter defining the distal slot of the tip aperture and a second portion of the rigid outer perimeter defining the open area of the tip aperture, the distal slot having a slot length that extends past the eyelash deflectors; and
  attaching the prosthesis to the candidate eyelash while the candidate eyelash is disposed in the open area of the tip aperture.

12. The method as described in claim 11, further comprising applying an adhesive to a portion of the prosthesis, the adhesive disposed in an adhesive reservoir of the instrument.

13. The method as described in claim 11, further comprising removing the prosthesis from a prosthesis strip of a prostheses repository of the instrument.

14. The method as described in claim 11, further comprising preventing a rotational movement of the instrument about a central axis of a handle of the instrument, the rotational movement prevented by a geometry of a portion of the instrument.

15. The method as described in claim 11, further comprising:
  actuating the instrument tip; and disposing an additional candidate eyelash in the tip aperture and attaching an additional prosthesis to the additional candidate eyelash while the additional candidate eyelash is disposed in the tip aperture.

16. The method as described in claim 15, wherein the additional prosthesis has a length that is different from a length of the prosthesis.

17. The method as described in claim 11, further comprising:
applying a force to a superior portion of the candidate eyelash; and
actuating the candidate eyelash until the candidate eyelash is inferior to a plane having the eyelashes adjacent to the candidate eyelash.

18. An instrument for isolating a candidate eyelash from adjacent eyelashes, the instrument comprising:
a handle having a handle distal end and a handle proximal end;
an instrument tip having a rigid outer perimeter and a tip aperture within the rigid outer perimeter, the tip aperture including a distal slot having a slot width configured to receive the candidate eyelash, the rigid outer perimeter configured to apply a force to the adjacent eyelashes;
distal deflectors of the instrument tip configured to deflect the adjacent eyelashes away from the candidate eyelash if the adjacent eyelashes are separated by a distance that is less than a width of a portion of the instrument tip that encloses the distal slot;
a prostheses repository including first prosthesis strip having a first prosthesis and a second prosthesis strip having a second prosthesis, the first prosthesis having a first length and the second prosthesis having a second length; and
an adhesive reservoir disposed between the instrument tip and the prostheses repository, the adhesive reservoir configured to house an adhesive.

19. The instrument as described in claim 18, further comprising a flat portion of an outer surface of the instrument, the flat portion configured to prevent rotational movement of the instrument.

20. The instrument as described in claim 18, wherein the rigid outer perimeter has a portion that defines an open area of the tip aperture, the open area having a variable width.

* * * * *